(12) United States Patent
Vigliotti et al.

(10) Patent No.: US 10,342,676 B2
(45) Date of Patent: Jul. 9, 2019

(54) APPARATUS FOR LOCATING THE POSITION OF A SPINAL IMPLANT DURING SURGERY

(71) Applicant: SPINE WAVE, INC., Shelton, CT (US)

(72) Inventors: Daniel Vigliotti, Guilford, CT (US); Andrew Penfold, Milford, CT (US)

(73) Assignee: SPINE WAVE, INC., Shelton, CT (US)

( * ) Notice: Subject to any disclaimer, the term of this patent is extended or adjusted under 35 U.S.C. 154(b) by 261 days.

(21) Appl. No.: 15/350,566

(22) Filed: Nov. 14, 2016

(65) Prior Publication Data

US 2017/0071751 A1 Mar. 16, 2017

Related U.S. Application Data

(62) Division of application No. 14/295,780, filed on Jun. 4, 2014, now Pat. No. 9,498,351.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/3008* (2013.01); *A61F 2002/30774* (2013.01); *A61F 2002/4475* (2013.01); *A61F 2002/4627* (2013.01); *A61F 2002/4629* (2013.01)

(58) Field of Classification Search
CPC ...... A61F 2/447; A61F 2/4603; A61F 2/4611; A61F 2002/4625; A61F 2002/4627; A61B 17/88
See application file for complete search history.

(56) References Cited

U.S. PATENT DOCUMENTS

| 9,687,356 | B1 * | 6/2017 | Spangler | A61F 2/4455 |
| 2006/0293748 | A1 * | 12/2006 | Alexander | A61F 2/447 623/17.11 |
| 2011/0230965 | A1 * | 9/2011 | Schell | A61F 2/447 623/17.11 |

* cited by examiner

*Primary Examiner* — Matthew J Lawson
*Assistant Examiner* — Amy R Sipp
(74) *Attorney, Agent, or Firm* — Hoffmann & Baron, LLP

(57) ABSTRACT

An apparatus and method for locating the position of a spinal implant in an intradiscal space patient during surgery, comprising a spinal implant formed of radiolucent material and a releasably attached inserter comprising a positioning element including thereon a marker of material more radiopaque than the material of the spinal implant. The positioning element extends into the implant such that the marker is positioned at a predetermined location within the implant, the positioning element with the radiopaque maker being removable from the spinal implant after insertion. In a particular method of locating the position of the spinal implant, the spinal implant is inserted from the lateral approach.

4 Claims, 5 Drawing Sheets

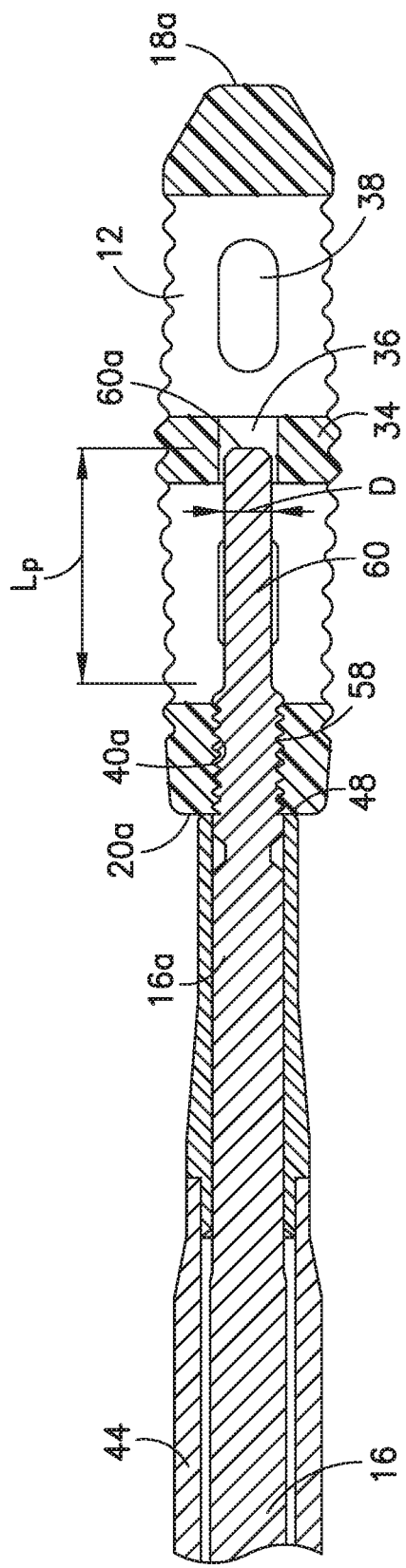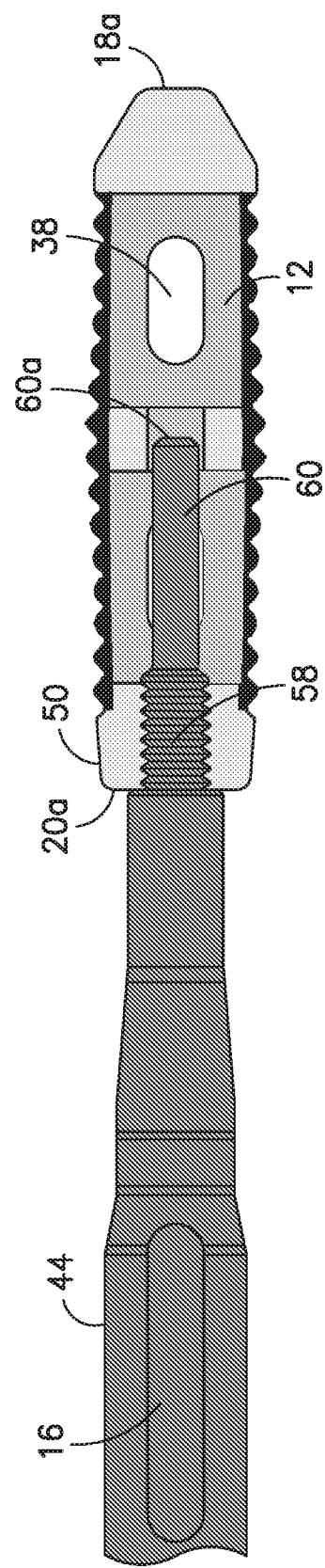

APPARATUS FOR LOCATING THE POSITION OF A SPINAL IMPLANT DURING SURGERY

FIELD OF THE INVENTION

The subject invention relates generally to the field of spinal implants and more particularly to instruments and methods for locating with imaging techniques the position of such implants during insertion into a patient.

BACKGROUND OF THE INVENTION

Implants such as spinal interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone or bone substitute material is placed substantially in and/or adjacent the device in order to promote fusion between two adjacent vertebrae.

Spinal fusion devices may be inserted during a spinal surgical procedure using an anterior, posterior, posterior lateral, lateral or extrapedicular approach. Examples of expandable spinal interbody fusion devices are described in U.S. Pat. No. 6,595,998 entitled "Tissue Distraction Device", which issued on Jul. 22, 2003 (the '998 Patent) and U.S. Pat. No. 7,967,867 entitled "Expandable Interbody Fusion Device", which issued on Jun. 28, 2011 (the '867 Patent). Spinal fusion devices may also be non-expandable, monolithic devices of fixed dimension, as shown for example, in U.S. Pat. No. 7,749,269 which issued on Jul. 6, 2010 and is assigned on its face to Warsaw Orthopedic, Inc. (the '269 Patent) and U.S. Pat. No. 7,918,891 which issued Apr. 5, 2011 and is assigned on its face to NuVasive Inc. (the '891 Patent). The spinal fusion devices described in the '269 Patent and the '891 patent are particularly configured for insertion into the intradiscal disc space from the lateral approach, with such implants having a length that when positioned in the disc space from one lateral side to the other the implant may rest on the cortical rims of both opposing lateral sides of a vertebral body.

One of the issues facing a surgeon during spinal surgery is the proper positioning of the implant in the intradiscal disc space. Spinal fusion implants are frequently made of materials such as polyetheretherketone polymer (PEEK) for strength and other biocompatible properties. However, since such materials are often radiolucent they are difficult to visualize under X-rays or fluoroscopy. To enable visualization, a radiopaque material such as a metal marker or barium sulfate may be combined with the implant material when the implants are manufactured, such as described in the '998 Patent. Visualization elements may also be provided in the form of spike elements or pins located at the proximal and distal ends of the implant as well as in a medial support between fusion apertures, as shown, for example, in the '891 Patent.

While such known visualization have been generally satisfactory, there nevertheless remains a need for improvements in surgical techniques to assist the surgeon in determining the proper position of a spinal implant during the implantation procedure.

SUMMARY OF THE INVENTION

It is an object of the invention to provide an apparatus and method for locating the position of a spinal implant in an intradiscal space patient during surgery, comprising a spinal implant formed of radiolucent material and a releasably attached inserter comprising a positioning element including thereon a marker of material more radiopaque than the material of the spinal implant, the positioning element extending into the implant such that the marker is positioned at a predetermined location within the implant, the positioning element with the radiopaque maker being removable from the spinal implant after insertion. In a particular method of locating the position of the spinal implant, the spinal implant is inserted from the lateral approach.

It is a further object of the invention to provide a kit of parts comprising an inserter, a plurality of spinal implants each of which has a different maximum length, and a plurality of positioning elements each of which is adapted to be individually supported by the inserter for extending into a correlated implant, each of the plurality of positioning elements having a radiopaque marker thereon at a different location.

DESCRIPTION OF THE FIGURES

FIG. 5 is a longitudinal cross-sectional view of the end of the assembled inserter of FIG. 1 attached to the spinal implant.

FIG. 6 is a side elevation view of the distal end of the inserter attached to the spinal implant similar to that of FIG. 6 showing the enhanced visualization characteristics of an embodiment of the subject invention under fluoroscopy.

DESCRIPTION OF THE EMBODIMENTS

Figure 1:
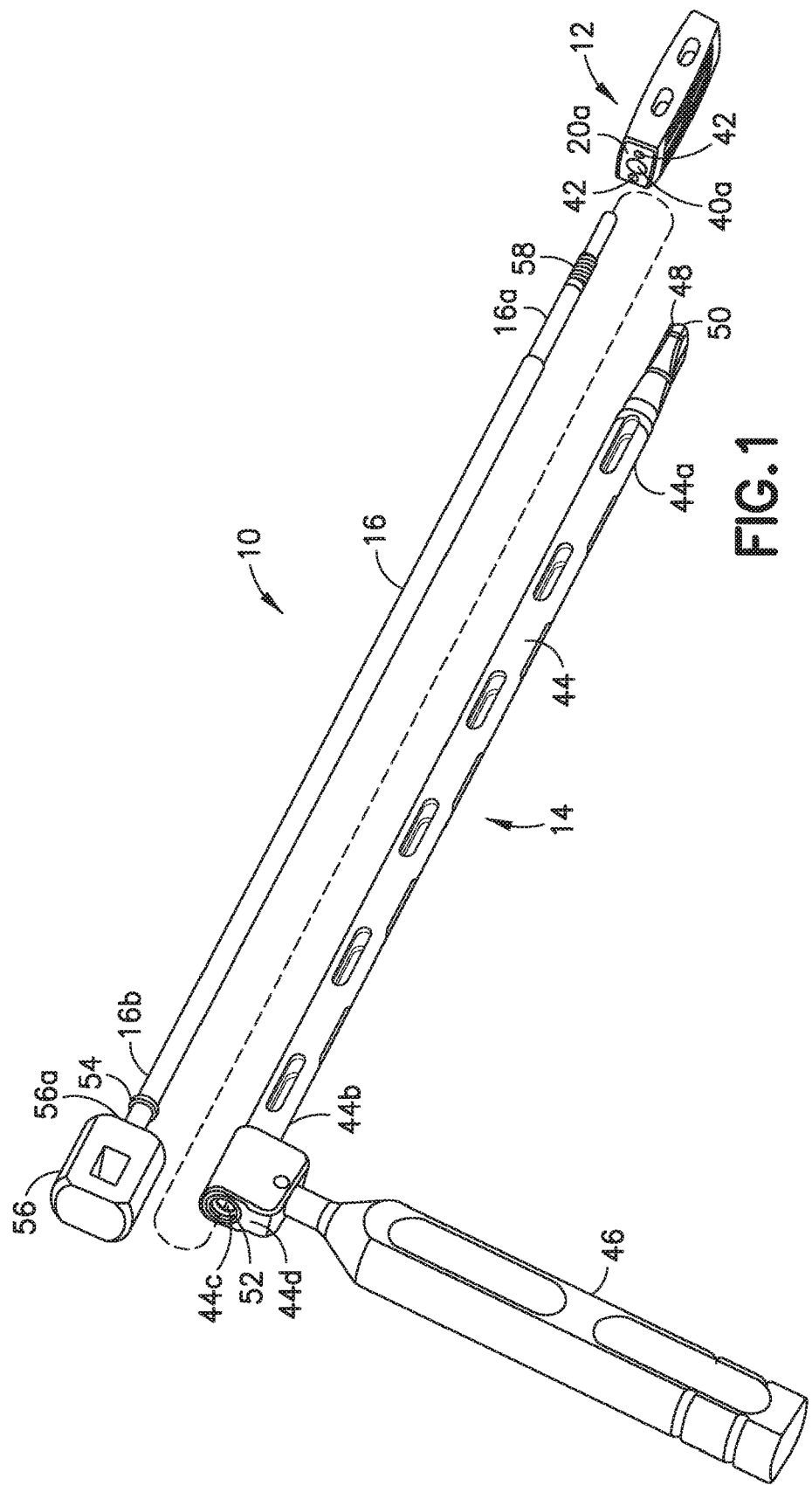
FIG. 1 is an exploded perspective view of an apparatus according to an embodiment of the subject invention for locating the position of the spinal implant during surgery showing the spinal implant and components of the implant inserter.

For the purposes of promoting an understanding of the principles of the invention, reference will now be made to the drawing figures and the following written description. It is understood that no limitation to the scope of the invention is thereby intend. It is further understood that the present invention includes any alterations and modifications to the illustrated arrangements and further includes applications of principles of the invention as would normally occur one skilled in the art to which this invention pertains.

Referring now to FIGS. 1-4, there is shown an apparatus 10 that includes a spinal implant 12 and an inserter 14 for locating the position of spinal fusion implant 12 in a patient during surgery. In this particular arrangement, spinal implant 12 has a bi-convex configuration for use in interbody spinal fusion and is introduced into the intradiscal space between two opposing vertebral bodies of a patient from the lateral approach. It should be appreciated however, that spinal implant 12 may also be configured for other applications and may be inserted during a spinal surgical procedure using an anterior, posterior, posterior lateral, or extrapedicular approach. Inserter 14 includes an elongate connection rod 16 for releasably connecting inserter 14 to spinal implant 12 and for assisting in locating the position of spinal implant 12 in the intradiscal space, as will be further described.

Figure 2:
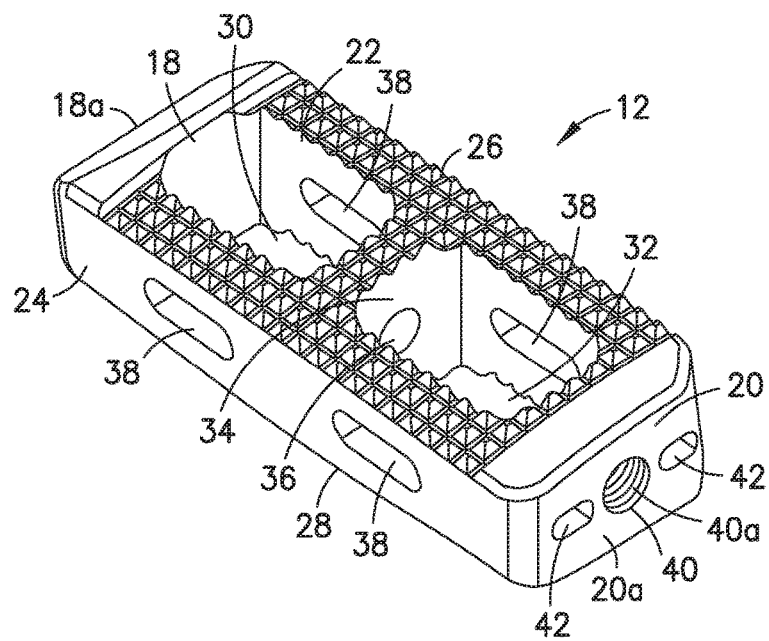
FIG. 2 is a top perspective view of the spinal implant of FIG. 1.
Figure 3:
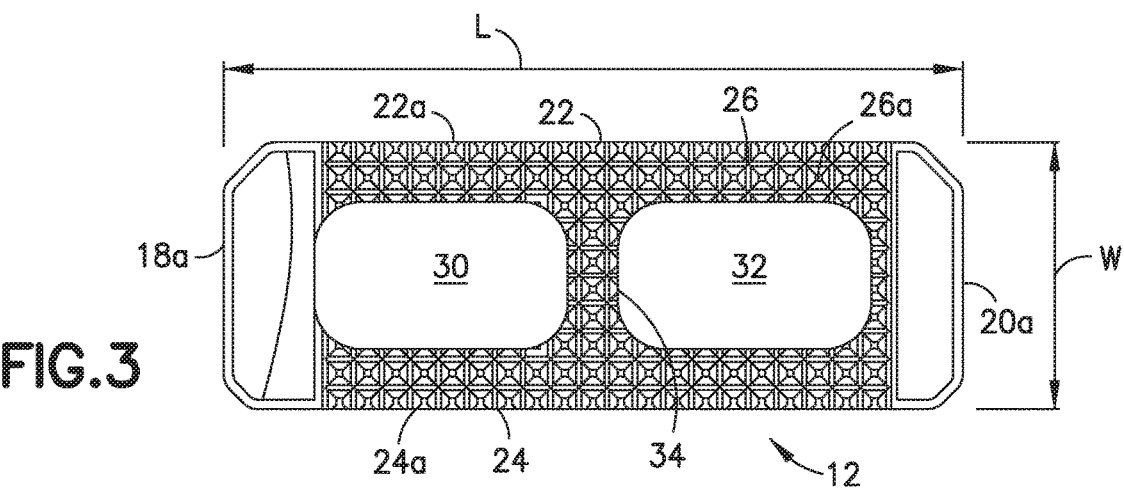
FIG. 3 is a top plan view of the spinal implant of FIG. 2
Figure 4:
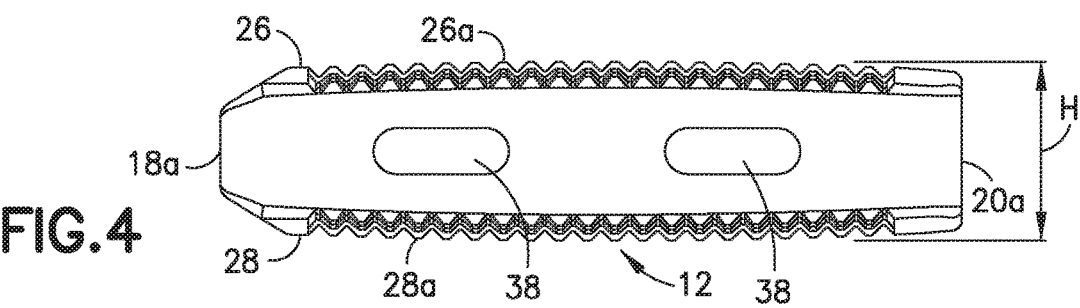
FIG. 4 is a side elevation view of the spinal implant of FIG. 2.

Turning now to FIGS. 2-4, details of spinal implant 12 are set forth. Spinal implant 12 is generally of parallelepiped configuration comprising a distal front wall 18, a spaced opposed proximal rear wall 20 and a pair of spaced opposed sidewalls 22 and 24 extending between front wall 18 and rear wall 20. In this arrangement, front wall 18 and rear wall 20 and generally parallel to each other with sidewalls 22 and 24 being generally parallel to each other. Front wall 18 includes a distal leading surface 18a and rear wall 20 includes a proximal trailing surface 20a. Implant 12 includes a top surface 26 and a bottom surface 28 each of which may be formed in a preferred arrangement to have a convex configuration between front wall 18 and rear wall 20 as well as being convex between sidewalls 22 and 24. Top surface 26 and bottom surface 28 may also be formed to each include pyramidal configurations 26a and 28a, or other surface features, such as saw-teeth and serrations, to provide resistance against expulsion of spinal implant 12 once inserted into the intradiscal space.

In the particular arrangement of spinal implant 12, a pair of fusion apertures 30 and 32 is formed through the top surface 26 and bottom surface 28, apertures 30 and 32 being separated an intermediate wall 34, wall 34 being generally parallel to front wall 18 and rear wall 20. In a particular arrangement, intermediate wall 34 is located approximately midway between said leading surface 18a and said trailing surface 20a of spinal implant 12. It should be appreciated however, that spinal implant 12 may also be formed to have a single fusion aperture or more than two apertures separated by one or more intermediate walls 34. Front fusion apertures 30 and rear fusion aperture 32 are provided to be filled with appropriate bone growth promotion material to enhance fusion between opposing vertebral bodies. Intermediate wall 34 has an opening 36 extending therethrough in communication with apertures 30 and 32 to allow bone growth promotion material to flow therethrough and to further serve in the positioning of spinal implant 12 during insertion, as will be described. Sidewalls 22 and 24 may also be formed to have windows 38 extending therethrough in communication with respective apertures 30 and 32 for further flow of bone growth promotion material into and through spinal implant 12. Windows 38 further provide assistance in the visualization of the positioning of spinal implant 12 during insertion. Rear wall 20 is further formed to have an opening 40 extending therethrough, opening 40 communicating with rear aperture 32. Opening 40 is formed to have internal threads 40a for threaded engagement with rod 16, as will be described. Rear wall 20 is further provided with a pair of laterally extending slots 42 extending into proximal trailing surface 20a for engagement with protrusions on the distal end of the inserter 14 for stabilizing the spinal implant 12 against rotation during insertion, as will be set forth.

In the particular parallelepiped configuration being described, spinal implant 12 has an overall maximum length L, a height H and a width W, as depicted in FIGS. 2-3. The maximum length L is defined by the distance between distal leading surface 18a and proximal trailing surface 20a. The height H is defined by the maximum distance between the apices is of the top surface 26 and bottom surface 28. The width W is defined by the maximum distance between the exterior surfaces 22a and 24a of sidewalls 22 and 24, respectively. For use as an interbody fusion implant inserted from the lateral aspect, spinal implant 12 has in a particular arrangement, a maximum length L of 50 mm, a height H of 8 mm, and a width W of 18 mm. However, for use as an interbody fusion implant from the lateral aspect, spinal implant 12 may have a maximum length L ranging from 40 mm to 60 mm, a height H ranging from 6 mm to 16 nm, and a width W ranging from 14 mm to 26 mm. It should be appreciated however, that when spinal implant 12 is used in interbody fusion applications inserted from other than the lateral aspect, such as with an anterior, posterior, posterior lateral or extrapedicular approach, the spinal implant 12 may be formed to have dimensions suitable for such applications.

In the particular arrangement described, spinal implant 12 is formed of polyetheretherketone polymer (PEEK) for its strength and other biocompatible properties. Other suitable biocompatible materials may be used for spinal implant 12, including but not limited to, polyetherketoneketone (PEKK) and other polymeric materials. However, such materials are typically radiolucent and difficult to visualize under imaging techniques, such X-rays or fluoroscopy.

Referring again to FIG. 1 as well as to FIG. 5, details of the inserter 14 are described. Inserter 14 comprises an elongate hollow barrel 44 having a distal end 44a and a proximal end 44b. A lumen 44c extends fully centrally through barrel 44, lumen 44c being configured and sized for receipt of elongate connection rod 16 therethrough. A handle 46 is suitably attached to the proximal end 44b of barrel 44. The distal end 44a defines a contact surface 48 for contacting proximal (railing surface 20a of spinal implant 12 when inserter 14 is releasably attached to spinal implant 12. A pair of laterally spaced protrusions 50, in the form, for example, of pins having bullet shaped noses project axially from contact surface 48, protrusions 50) being configured and sized to be received into slots 42 of trailing surface 20a of spinal implant 12 during attachment of inserter 14 thereto. At the proximal end 44b of barrel 44 a threaded internal opening 52 is provided for threaded releasable attachment to elongate rod 16, as will be described. Barrel 44 may be formed of a suitable metal, such as stainless steel, or other suitably rigid material.

Elongate connection rod 16 has a distal end 16a and a proximal end 16b. Proximal end 16b is externally threaded for an axial extent 54, threaded extent 54 providing a connector that is configured for releasable threaded engagement into threaded internal opening 52 of barrel 44. A knob 56 is provided at the distalmost end 16b of elongate rod 16, knob 56 being suitable for handling rod 16 during connection of inserter 14 to spinal implant 12. Distal end 16a is externally threaded for an axial portion 58, threaded portion 58 providing a connector that is configured for releasable threaded engagement into threaded opening 40a in the rear wall 20 of spinal implant 12.

As illustrated in FIG. 5, the distal end 16a of elongate rod 16 comprises a positioning element 60 projecting for an extent axially distally of threaded portion 58. Positioning element 60 and in a particular arrangement is generally cylindrical having a length $L_P$ and a diameter D. It should be appreciated that other configurations of positioning element 60 may be provided, such as but not limited to, square, rectangular or tapering configurations. Positioning element 60 has at its distalmost end a substantially flat end surface 60a, which as will be described serves as a marker for assisting in the positioning of implant 12 into the intradiscal space. The axial dimension of length $L_P$ is provided such that end surface 60a lies within the spinal implant 12 between leading surface 18a and trailing surface 20a at a predetermined distance from contact surface 48 of barrel 44. In the particular arrangement being described, the diameter D of positioning element 60 is configured to be received within opening 36 of intermediate wall 34 and length $L_P$ is formed such that end surface 60a resides approximately midway into opening 36 of intermediate wall 34. As such, end surface 60a in this arrangement would establish the approximate axial midpoint between leading surface 18a and trailing surface 20a of spinal implant 12. It should be appreciated however, that the pre-determined distance surface 60a extends from the contact surface 48 of barrel 44 may be other than the axial midpoint of spinal implant 12.

In accordance with the subject matter of the invention, the positioning element is formed of a material more radiopaque than the material of spinal implant 12. In a particular arrangement, positioning element 60 is formed of stainless steel, although other suitable radiopaque materials may be provided. In one particular embodiment, the entire elongated rod 16, including the positioning element 60 is formed integrally as a one-piece rod of stainless steel.

Under suitable imaging techniques, such as with fluoroscopy or X-rays, the contrast between the radiopaque positioning element 60 and the radiolucent spinal implant 12 maybe readily observed, as shown in FIG. 6. End surface 60a of positioning element 60 serves as a radiopaque marker clearly denoting in this particular arrangement the axial center point of spinal implant 12 between leading surface 18a and trailing surface 20a.

While the radiopaque marker described herein is particularly defined by substantially flat end surface 60a with the positioning element being formed of radiopaque material, it should be appreciated that a radiopaque marker may be provided in a different manner within the context of the subject invention. For example, the radiopaque marker may be provided by a relatively sharp tip or apex of a curved surface at the distalmost end of the positioning element 60. The radiopaque marker may also be provided by a hole through the positioning element 64 or a stripe of material less radiopaque than the material of positioning element 60. Further, positioning element 60 may be formed of radiolucent material with a bead, coating or other deposit of radiopaque material thereon. In each instance, the radiopaque marker would be located on positioning element 60 such that when inserter 14 is attached to spinal element 12 the radiopaque marker is located within spinal implant 12 at the predetermined distance from contact surface 48 of barrel 44.

The preparation for inserting spinal implant 12 from the lateral approach including the establishment of a surgical corridor through the tissue to the spine is more particularly described in commonly owned U.S. patent application Ser. No. 14/342,563, entitled "Lateral Approach Expandable Spinal Implant and Method", filed on Mar. 4, 2014 by Peter Barreiro and published internationally as WO 2013/036707, the entire contents of which are incorporated herein by reference. Having completed the proper preparation and access for the lateral approach, the method of locating the position of spinal implant 12 from the lateral approach is now described.

A kit of parts may be provided to the surgeon comprising inserter 14, a set of different size spinal implants 12 at least having different lengths L, and a set of elongate rods 16 at least having different positioning element lengths $L_P$. The rods 16 may be correlated with the spinal implants 12 so as to match their respective lengths, such correlation being provided by color coding or other suitable matching indicia. Upon selection of a spinal implant 60 having a desired length L for the particular surgery and a rod 16 having a positioning element 60 suitable for determining the axial midpoint of spinal implant 12, inserter 14 may be attached to the chosen spinal implant 12 by the chosen rod 16.

Referring again to FIG. 1, the selected rod 16 is inserted through lumen 44c of barrel 44 so that threaded extent 54 at the proximal end 16b of rod 16 threadably engages the threaded opening 52 at the proximal and 44b of barrel 44. As such, rod 16 is releasably attached to barrel 44. At this stage, the distal end 16a, including threaded portion 58 and positioning element 60 project distally outwardly of contact surface 48 of barrel 44. Positioning element 60 is introduced into opening 40a through the rear wall 20 of spinal implant 12 until the threads of threaded portion 58 threadably engage the threads of threaded opening 40a. The surgeon continues to thread the threaded portion 58 into the spinal implant using knob 56 until the back distal surface 56a of knob 56 contacts the proximal end surface 44d of barrel 44, as illustrated in FIG. 1. Once fully tightened, barrel 44 is compressed between back distal surface 56a of knob 56 and trailing surface 20a of spinal implant 12. During such assembly, barrel protrusions 50 engage with slots 42 in trailing surface 20a for stabilizing the spinal implant 12 against rotation during insertion. At this stage as illustrated in FIG. 5, barrel 44, rod 16 and spinal implant 12 are fully assembled with end surface 60a being disposed within intermediate wall 34, thereby establishing the axial midpoint of spinal implant 12 between leading surface 18a and trailing surface 20a.

Figure 7:
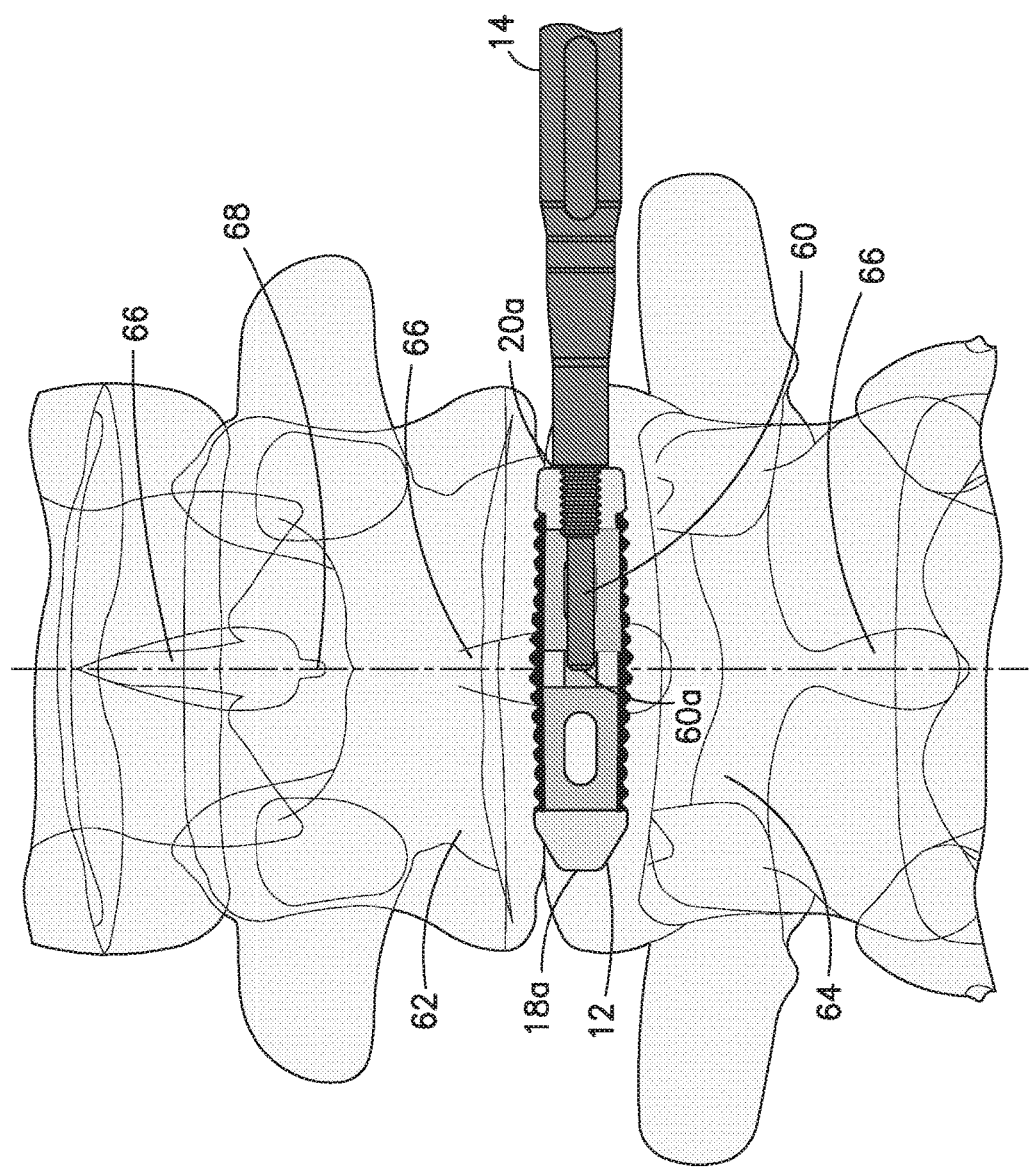
FIG. 7 is a side elevation view similar to that of FIG. 6 showing the introduction of a spinal implant into the intradiscal space of a spine from the lateral approach under fluoroscopy.

The implant 12 is then introduced into the prepared intradiscal space between two vertebral bodies 62 and 64 as shown in FIG. 7. Using fluoroscopy, certain anatomical features of the spine such as the spinous processes 66 are discernible due to their bony characteristics. The progress of the insertion of spinal implant 12 may be monitored under fluoroscopy until the end surface 60a of positioning element 60 is substantially aligned with the anatomical center of spinous processes 66 in the cephalad-caudad direction. As such, the axial midpoint of spinal implant 12 is properly centered in the intradiscal space relative to the sagittal plane of the patient by reference to the spinous processes. Once proper positioning is achieved, the surgeon may remove the inserter 14 by unthreading rod 16 from spinal implant 12, separating rod 16 and barrel 44 from spinal implant 12, and leaving spinal implant 12 properly positioned in the intradiscal space. It should be appreciated that while using the spinous processes 68 is suitable for centering spinal implant 12 in the intradiscal space from the lateral aspect, other anatomical features, such as the dense cortical rims, be used for locating the position of a spinal implant, in particular, where insertion is an approach other than the lateral aspect.

Figure 8:
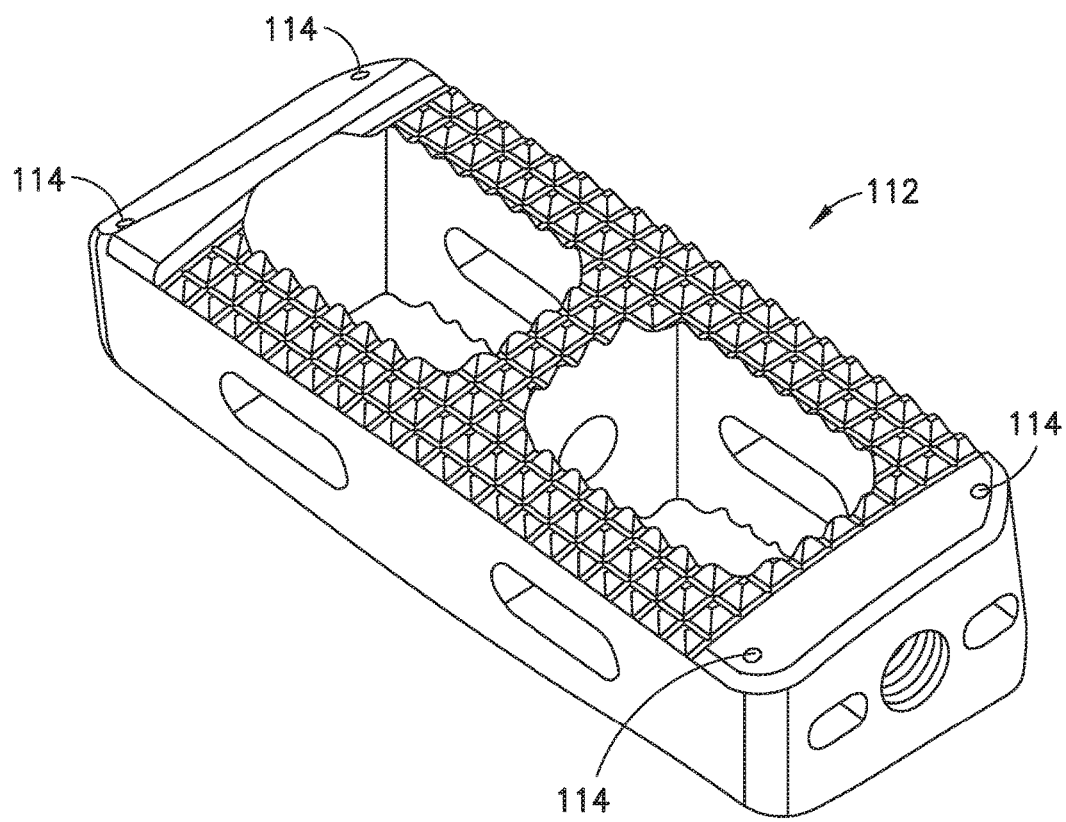
FIG. 8 is a top perspective view of an alternative arrangement the spinal implant of FIG. 2.

Having described the particular arrangement of the apparatus 10 and method for locating the position of spinal fusion implant 12 in a patient during surgery, it should be appreciated that variations may be made thereto without deviating from the contemplated scope of the invention. For example, while the spinal implant 12 can be positioned into the intradiscal space such that the axial midpoint of spinal implant 12 is centered relative to the sagittal plane without the need for radiopaque elements within spinal implant 12, additional features may be desirable to determine different positions or orientations during insertion. As such, spinal implant 112, which may be otherwise identical to spinal implant 12, may be provided with one or more radiopaque markers 114, as depicted in FIG. 8. Markers 114 may be permanently contained, for example, within the corners of spinal implant 112, each marker 114 being configured in the form of a pin or post having a length that extends downwardly into spinal implant 112. With such pins 114, and from the fluoroscopic view of FIG. 7, the surgeon would be able to determine whether spinal implant 112 has rotated within the plane of the intradiscal space such that the axial centerline of spinal implant 114 is not generally perpendicular to the sagittal plane as desired. Suitable corrections may then be made.

Figure 9:
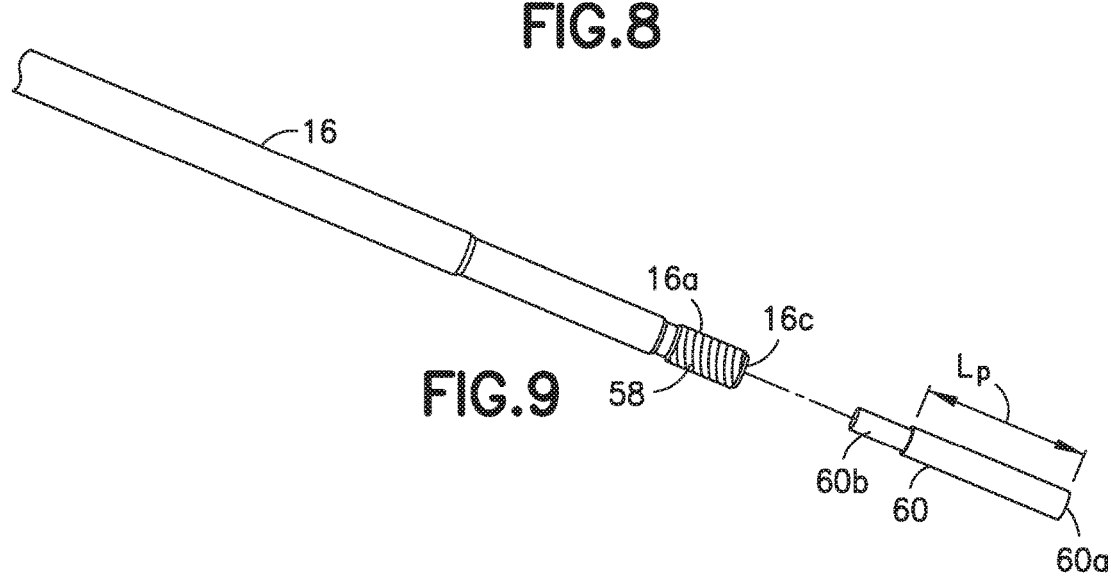
FIG. 9 is an perspective view of an alternative arrangement wherein a positioning element useful in the apparatus of FIG. 1 is formed as a separate piece suitably attachable to the distal end of elongate rod of the apparatus.

In another variation, positioning element 60, instead of being formed integrally as a one piece unit with elongate connection rod 16, may be formed as a separate piece suitably attachable to the distal end 16a of elongate rod 16, as illustrated in FIG. 9. The proximal end 60b of positioning element 60 may have an external thread for receipt into an internally threaded opening 16c extending into the distal end 16a of rod 16. It should be appreciated that other suitable joining structure, such as a press fit, may also be used to separably attach positioning element 60 to rod 16. A set of separate positioning elements 60 may be provided to the surgeon in the kit of parts, with each positioning element 60 having a different length $L_P$ that is correlated respectively to a length of the different spinal implants 12 in the kit. Each of the positioning elements 60 may be entirely formed of radiopaque material, such as stainless steel. In this arrangement, only a single elongate connection rod 16 would be necessary. Accordingly, the arrangements described herein are intended to be illustrative and not limiting.

What is claimed is:

1. A method of locating a position of a spinal implant during surgery for interbody fusion with reference to a feature of spinal anatomy, comprising steps of:

providing a spinal implant formed of radiolucent material having a distal leading surface and a proximal trailing surface, said spinal implant having two fusion apertures therethrough divided by an intermediate wall, said intermediate wall having therethrough an opening communicating with each of said apertures;

releasably attaching to said spinal implant an inserter having a positioning element projecting distally therefrom along an axis, said positioning element defining a radiopaque marker, said radiopaque marker being positioned interiorly of said spinal implant within the opening of said intermediate wall, said marker being disposed so as to define a line of demarcation within the opening of said intermediate wall and discernible in a view transverse to said axis and configured for identification of an axial point between said leading surface and said trailing surface;

introducing said spinal implant by said inserter into an intradiscal space between two opposing vertebral bodies;

using an imaging technique and with reference to a feature of the spinal anatomy, inserting said spinal implant into said intradiscal space until said radiopaque marker is positioned in said intradiscal space relative to said feature of spinal anatomy; and removing said inserter with said radiopaque marker thereon from said spinal implant and leaving said spinal implant in said intradiscal space.

2. The method of claim 1, wherein said spinal implant is inserted from a lateral approach and the spinal anatomical reference is to spinous processes, and wherein said spinal implant is inserted into said intradiscal space until said radiopaque marker is positioned generally in alignment with said spinous processes in a cephalad-caudad direction.

3. The method of claim 2, wherein said intermediate wall is approximately midway between said leading surface and said trailing surface.

4. The method of claim 3, wherein said marker is defined by a distal-most surface of said positioning element and wherein said positioning element is formed of radiopaque material, said distal-most surface being discernible with said imaging technique in relation to said spinous processes.

* * * * *